United States Patent
Simonov et al.

(10) Patent No.: US 9,114,005 B2
(45) Date of Patent: Aug. 25, 2015

(54) ACCOMMODATIVE INTRAOCULAR LENS DRIVEN BY CILIARY MASS

(75) Inventors: Aleksey Nikolaevich Simonov, The Hague (NL); Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 0 days.

(21) Appl. No.: 13/510,132

(22) PCT Filed: Nov. 17, 2010

(86) PCT No.: PCT/NL2010/050766
§ 371 (c)(1),
(2), (4) Date: Aug. 24, 2012

(87) PCT Pub. No.: WO2011/062486
PCT Pub. Date: May 26, 2011

(65) Prior Publication Data
US 2012/0310341 A1    Dec. 6, 2012

(30) Foreign Application Priority Data
Nov. 17, 2009  (NL) .................................... 2003816

(51) Int. Cl.
*A61F 2/16*    (2006.01)

(52) U.S. Cl.
CPC ............. *A61F 2/1613* (2013.01); *A61F 2/1635* (2013.01); *A61F 2/1648* (2013.01)

(58) Field of Classification Search
USPC ....................................................... 623/6.37
See application file for complete search history.

(56) References Cited

U.S. PATENT DOCUMENTS

| | | | |
|---|---|---|---|
| 5,275,623 A | 1/1994 | Sarfarazi | |
| 5,674,282 A | 10/1997 | Cumming | |
| 6,197,059 B1 | 3/2001 | Cumming | |
| 6,551,354 B1 * | 4/2003 | Ghazizadeh et al. | ........ 623/6.43 |
| 8,182,531 B2 | 5/2012 | Hermans et al. | |
| 2002/0107568 A1 | 8/2002 | Zadno-Azizi et al. | |
| 2003/0109925 A1 * | 6/2003 | Ghazizadeh et al. | ........ 623/6.34 |
| 2004/0215340 A1 | 10/2004 | Messner et al. | |
| 2007/0106377 A1 | 5/2007 | Smith et al. | |
| 2007/0108643 A1 | 5/2007 | Zadno-Azizi et al. | |
| 2008/0046076 A1 | 2/2008 | Rombach | |
| 2008/0215146 A1 | 9/2008 | Rombach | |

(Continued)

FOREIGN PATENT DOCUMENTS

| | | |
|---|---|---|
| WO | 0166042 A1 | 9/2001 |
| WO | 2005084587 A2 | 9/2005 |

(Continued)

OTHER PUBLICATIONS

Bernet et al. "Adjustable refractive power from diffractive moiré elements". Applied Optics. Jul. 20, 2008. pp. 3722-3730.vol. 47, No. 21.

*Primary Examiner* — David H Willse
*Assistant Examiner* — Tiffany Shipmon
(74) *Attorney, Agent, or Firm* — The Webb Law Firm

(57) ABSTRACT

The invention relates to an intraocular accommodative lens, comprising an optical arrangement and haptics, the lens being adapted for variable focusing by movement of at least one part of the optical arrangement by at least one of the haptics, wherein the haptics comprise a part adapted to transfer a movement from the ciliary mass to the optical arrangement. This forms an attractive way of driving the variable lens, in particular for locations of the lens avoiding the capsular bag.

3 Claims, 2 Drawing Sheets

(56) References Cited

U.S. PATENT DOCUMENTS

| | | |
|---|---|---|
| 2009/0062912 A1 | 3/2009 | Rombach |
| 2009/0264998 A1* | 10/2009 | Mentak et al. ............... 623/6.37 |
| 2010/0094413 A1 | 4/2010 | Rombach et al. |
| 2010/0106245 A1 | 4/2010 | Rombach et al. |
| 2010/0280609 A1 | 11/2010 | Simonov et al. |

FOREIGN PATENT DOCUMENTS

| | | |
|---|---|---|
| WO | 2006118452 A1 | 11/2006 |
| WO | 2008071760 A2 | 6/2008 |
| WO | 2008077795 A2 | 7/2008 |
| WO | 2008091152 A1 | 7/2008 |
| WO | 2009051477 A2 | 4/2009 |

* cited by examiner

ACCOMMODATIVE INTRAOCULAR LENS DRIVEN BY CILIARY MASS

BACKGROUND OF THE INVENTION

1) Field of the Invention

Accommodative intraocular lenses or, alternatively, accommodative lens constructions (henceforth: "accommodative lenses") are intended to replace the natural lens of the eye and restore its accommodative function. The accommodative lenses include an optical arrangement for variable focusing power ("focusing"), and, at least one, attachment component ("haptic") for positioning in the eye and actuating the optical arrangement by the eye muscles. For example, the haptic elements can covert the movement of the ciliary muscle into the movement of the optical arrangement. The lenses can be positioned either inside the capsular bag ("bag") or outside the bag. Accommodation is driven by the ciliary muscle ("muscle") via connecting tissues: the ciliary process and the zonulae. Ciliary mass, or, "mass", refers to the combination of said ciliary muscle, process, zonulae and supporting tissues.

2) Discussion of the Prior Art

In most current accommodative lenses the lens is positioned in the capsular bag and (1)—movement of the mass is transferred via the bag to the lens and, (2)—the bag separates lens and ciliary mass. In accommodative lenses described in this document (1)—movement of the ciliary mass is transferred directly to the lens and (2)—lens and ciliary mass are in direct contact.

The present invention concerns accommodative lenses, accommodative lens constructions, positioned outside the bag, at the plane of the mass, comprising an optical arrangement to vary the focusing power with at least one optical element and at least one haptic including at least one rim, which can be a flange for position in the sulcus and at least one coupling component and supporting components, with the coupling component adapted to transfer movement from the mass to the optical arrangement to contact the mass directly and to connect to at one end to the rim and at the other end to the optical arrangement. Hence the invention provides an accommodative lens construction including at least one optical arrangement adapted to vary its focusing power by movement of at least a part of the optical arrangement and at, least one haptic including at least one rim adapted to contact the mass of the eye and at least one coupling component connecting the rim to at least a part of the optical arrangement, wherein the haptic is adapted to transfer a movement from the mass to at least a part of the optical arrangement. A movement of a part of the optical arrangement is understood to encompass the deformation of said part of the optical arrangement. Further it is assumed that the movement of the rim, especially when it is monolithic, will incorporate the deformation of the rim and possibly the coupling component.

Optical arrangements for variable focusing may include effecting at least one optical element. This implies movement of at least one moving optical element, or deformation of at least one optical element having variable shape. The movements can be: (i) axial movements ("translations"), i.e. along the optical axis of the accommodative lens, as, for example, in US2002107568, US2007108643, US2004215340, U.S. Pat. No. 6,197,059, U.S. Pat. No. 5,674,282, or U.S. Pat. No. 5,275,623; (ii) lateral movements ("shifts"), i.e. along a single axis perpendicular to the optical axis, as disclosed, for example, in U.S. 2008/046,076, WO2008,091,152, WO2009, 051,477, U.S. 2008/215,146, U.S. 2009/062,912, WO2006, 118,452 and WO2008,071,760; (iii) rotational movements ("rotations") of the fan-like rotating surfaces as disclosed, for example, in WO2005,084,587 and WO2008,077,795, the mathematical description of the surfaces is also given in Adjustable refractive power from diffractive moiré elements, S. Bernet and M. Ritsch-Marte, Appl. Opt. 47, 3722-3730, 2008. The variable shape, for example, variation of the radius of curvature of the optical element, can result from the mechanical deformation ("deformation") of the optical element or any part of it as described, for example, in US2007106377. The optical arrangement included in a lens construction should be adapted to employ any of the described mechanisms (translation, shift, rotation or deformation), as well as any combination of the described mechanisms, resulting in a variable focusing effect. The mechanism for variable focusing can be applied to, at least one, optical element.

SUMMARY OF THE INVENTION

The present invention concerns accommodative lenses, accommodative lens constructions, positioned outside the bag, at the plane of the mass, comprising an optical arrangement to vary the focusing power with at least one optical element and at least one haptic including at least one rim, which can be a flange for position in the sulcus and at least one coupling component and supporting components, with the coupling component adapted to transfer movement from the mass to the optical arrangement to contact the mass directly and to connect to at one end to the rim and at the other end to the optical arrangement. Hence the invention provides an accommodative lens construction including at least one optical arrangement adapted to vary its focusing power by movement of at least a part of the optical arrangement and at least one haptic including at least one rim adapted to contact the mass of the eye and at least one coupling component connecting the rim to at least a part of the optical arrangement, wherein the haptic is adapted to transfer a movement from the mass to at least a part of the optical arrangement. A movement of a part of the optical arrangement is understood to encompass the deformation of said part of the optical arrangement. Further it is assumed that the movement of the rim, especially when it is monolithic, will incorporate the deformation of the rim and possibly the coupling component.

BRIEF DESCRIPTION OF THE DRAWINGS

Subsequently the present invention will be elucidated with the help of the accompanying drawings, wherein show.

DETAILED DESCRIPTION OF THE PREFERRED EMBODIMENTS

Figure 1:
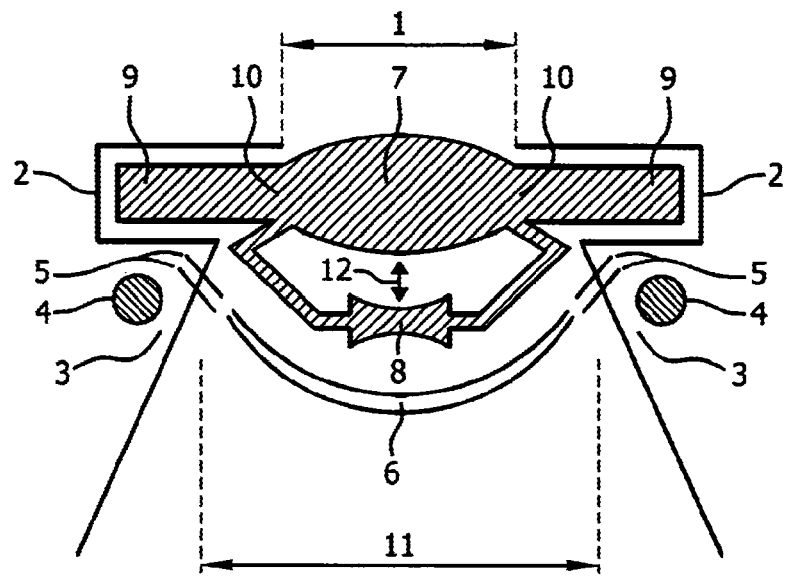
FIG. 1: a cross sectional view of a first embodiment comprising two translating optical elements in a position for emmetropia.

FIG. 1 shows an eye 1 of a human being, wherein the figure depicts the iris 2, the sulcus 3, the mass 4, muscles 5, process and zonulae and the capsular bag 6 of the eye. Further the drawing shows an accommodative lens, comprising an anterior optical element 7, a posterior optical element 8 and haptics, comprising a flange 9, a rim 10 and a coupling component, in this example a number of springs 16 connecting both optical elements 7, 8. Herein the flange 9 is adapted to extend in the sulcus 3 to provide fixation of the haptics and hence of the accommodative lens. In this embodiment the rim 10 is present as a part of the flange. The ciliary mass is adapted to contact the coupling element 16. Further an arrow 11 indicates the inter mass distance while an arrow 12 indicates the distance between the optical elements 7, 8 in the direction of the optical axis.

It will be clear that most parts of the accommodative lens, such as the optical elements 7, 8, have a substantial circular shape, but that the coupling element comprises a limited number, for instance two, three or four arms 16 functioning as springs and connecting both optical elements 7, 8. Further the rim 10 and the flange 9 may also extend over limited angular sectors of the full circle. The lens of this embodiment is of a type in which the optical strength varies with the distance between the optical elements 7, 8 in the direction of the optical axis. In the drawing the anterior optical element 7 has a positive optical strength while the posterior optical element 8 has a negative optical strength; it is however possible that both optical elements 7, 8 have a positive optical strength.

In the situation depicted in FIG. 1, the muscle 5 and the ciliary mass 4 are expanded, the lens 1 is relaxed, the distance between the optical elements 7, 8 is small and the accommodative power is low.

Figure 2:
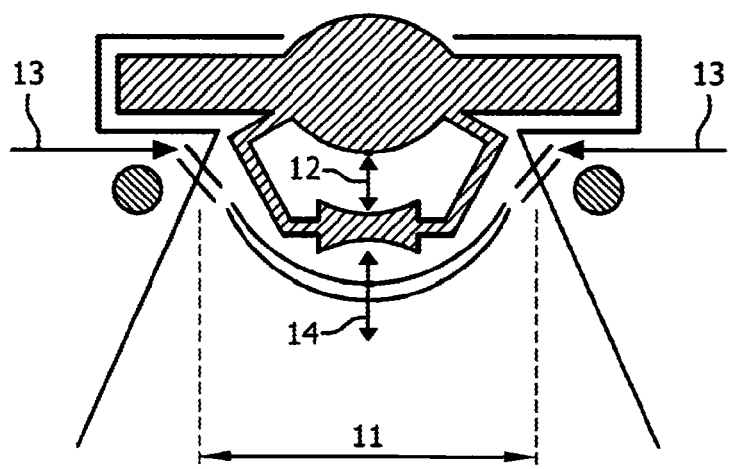
FIG. 2: a view similar to that of FIG. 1 in a position for accommodation.

The springs 16 are adapted to convey the movement of the ciliary mass to the posterior optical element, so that contraction of the ciliary mass leads to an axial movement of the posterior optical element 8 in the direction of the optical axis away from the anterior optical element 7. Herein it is noted that the it may be possible that the springs 16 or the rim 10 are not in contact with the ciliary mass when the ciliary mass is contracted. Then the ciliary mass would have to contract over a small path before contacting the springs or the rim and that after the ciliary mass has contacted the rim or springs the movement is transmitted. Then the situation depicted in FIG. 2 is obtained; herein the muscle 5 and mass 4 are contracted, the arms of the coupling component 16 are contracted and urge the posterior optical element 8 away from the anterior optical element 7 in the direction of the optical axis, so that the distance between the optical elements 7, 8 is large and the accommodative power is high.

Figure 3:
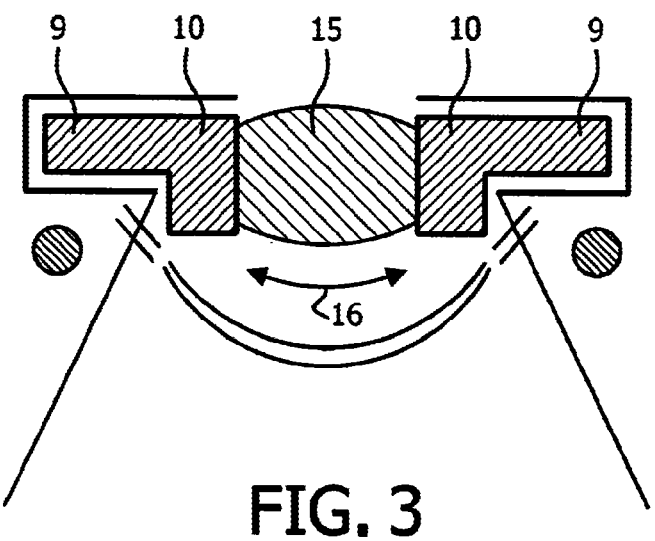
FIG. 3: a cross sectional view of a second embodiment comprising a deformable lens; in a position for emmetropia.

The embodiment depicted in FIG. 3 comprises a lens with a deformable optical element 15 only. Further the haptics are substantially different. In this embodiment the rim 10 is thicker than the flange 9, so that the rim 10 protrudes relative to the flange 9. The protruding flange 9 is contacted during contraction thereof, so that contraction of the ciliary mass applies a force to the flange and hence to the optical element 15. This optical element forms a lens of a kind wherein reduction of the radius leads to a bulging of the optical element 15, so that the lens obtains a higher optical strength. FIG. 3 shows the situation wherein the muscle 5 and ciliary mass 4 are expanded, the optical element 15 is relaxed with a large radius, so that it is relatively flat and the accommodative power of the lens is low.

Figure 4:
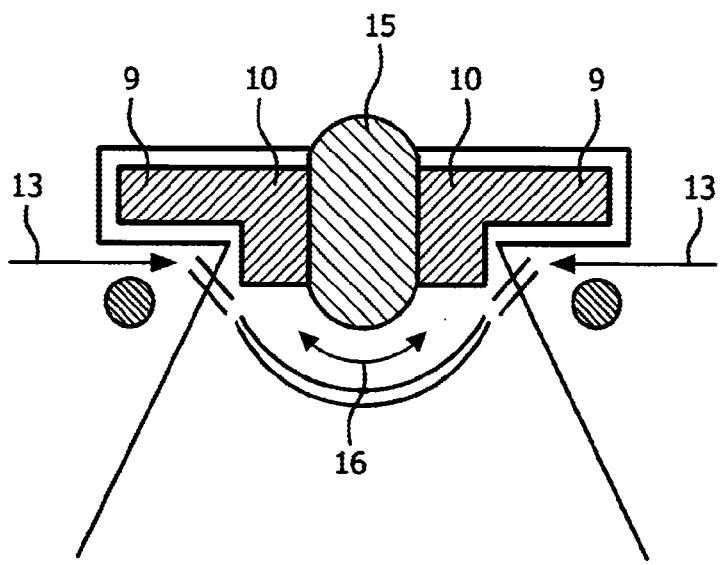
FIG. 4: a view similar to that of FIG. 3 in a position for accommodation.

FIG. 4 shows the same embodiment, but during accommodation. The muscle 5 and ciliary mass 4 are contracted, the optical element 15 is compressed by the haptics including the rim 10 of the haptics. Hence the optical element 15 has a small radius, and the accommodative power is high.

The above embodiments refer to different embodiments of haptic systems and to different embodiments of optical systems. The embodiments of haptic systems and of optical systems can be used in other combinations. It will be clear that the invention is also applicable to other lenses with variable focus, like lenses of the type wherein the mutual shifting of optical elements in the direction perpendicular to the optical axis leads to variation of the optical strength and lenses of the kind wherein mutual rotation will cause variation of the optical strength.

The invention claimed is:

1. An accommodative intraocular lens, comprising an optical arrangement and haptics, the lens being adapted for variable focusing by movement or deformation of at least one part of the optical arrangement by at least one of the haptics, wherein the haptics comprise a part adapted to transfer a movement from the ciliary mass to the optical arrangement,
   wherein the haptics comprise at least two springs adapted to transfer a movement from the ciliary mass to the optical arrangement,
   wherein the haptics comprise a coupling component which is adapted to contact the ciliary mass directly,
   wherein the haptics comprise a flange adapted for positioning in the sulcus,
   wherein the haptics further comprise a rim, said rim comprising a protruding part that is adapted to be in contact with the ciliary mass,
   wherein said rim is positioned between an anterior optical element and said flange, and each spring extends between said rim and a posterior optical element,
   wherein the springs are adapted to convey the movement of the ciliary mass to at least one optical element of the optical arrangement, to vary defocus by shift of said optical element, so that contraction of the ciliary mass leads to an axial movement of the posterior optical element in the direction of the optical axis, and
   wherein the axial movement of the posterior optical element corresponds to a change in diameter of the anterior optical element.

2. The accommodative intraocular lens of claim 1, wherein the springs have an angled structure.

3. An accommodative intraocular lens, comprising an optical arrangement and haptics, the lens being adapted for variable focusing by movement or deformation of at least one part of the optical arrangement by at least one of the haptics,
   wherein the haptics comprise a part adapted to transfer a movement from the ciliary mass to the optical arrangement,
   wherein the haptics comprise a coupling component which is adapted to contact the ciliary mass directly,
   wherein the haptics comprise a flange adapted for positioning in the sulcus,
   wherein the haptics further comprise a rim, said rim comprising a protruding part that is adapted to be in contact with the ciliary mass,
   wherein said rim is positioned between an anterior optical element and said flange, and
   wherein the accommodative intraocular lens is adapted to deform, at least one, optical element of the optical arrangement adapted to vary defocus by deformation of said optical element such that a change in diameter of the rim corresponds to a change in the optical power of the lens.

* * * * *